(12) United States Patent
Hallborn et al.

(10) Patent No.: US 6,582,944 B1
(45) Date of Patent: Jun. 24, 2003

(54) PRODUCTION OF ETHANOL FROM XYLOSE

(75) Inventors: Johan Hallborn, Lund (SE); Merja Penttilä, Helsinki (FI); Heikki Ojamo, Espoo (FI); Mats Walfridsson, Lund (SE); Ulla Airaksinen, Vantaa (FI); Sirkka Keränen, Helsinki (FI); Bärbel Hahn-Hägerdal, Lund (SE)

(73) Assignee: Xyrofin Oy, Helsinki (FI)

( * ) Notice: Subject to any disclaimer, the term of this patent is extended or adjusted under 35 U.S.C. 154(b) by 0 days.

(21) Appl. No.: 09/184,965

(22) Filed: Jan. 8, 1999

Related U.S. Application Data

(60) Division of application No. 08/336,198, filed on Nov. 3, 1994, now Pat. No. 5,866,382, which is a continuation of application No. 07/848,694, filed on Mar. 9, 1992, now abandoned, which is a continuation-in-part of application No. PCT/FI91/00103, filed on Apr. 8, 1991, which is a continuation-in-part of application No. 07/527,775, filed on May 24, 1990, now abandoned.

(30) Foreign Application Priority Data

Apr. 6, 1990 (FI) .................................... 901771

(51) Int. Cl.$^7$ .............................. C12P 7/06; C12N 1/19; C12N 1/15; C12N 9/02; C07H 21/04
(52) U.S. Cl. ............... 435/161; 435/254.11; 435/254.2; 435/254.21; 435/254.22; 435/254.23; 536/23.2
(58) Field of Search .......................... 435/41, 155, 157, 435/161, 163, 440, 483, 489, 254.11, 254.2, 254.21, 254.22, 254.23, 254.4; 536/23.2

(56) References Cited

U.S. PATENT DOCUMENTS 4,894,338 A  1/1990  Knowles et al. ........ 435/191.41

FOREIGN PATENT DOCUMENTS

| DE | 4009676 | 10/1991 |
| EP | 0450430 | 10/1991 |
| WO | 9115588 | 10/1991 |

OTHER PUBLICATIONS

Matsudaira (1991) Methods in Enzymology, vol. 182, pp. 602–613.*
Wozney (1991) Methods in Enzymology, vol. 182, pp. 738–751.*
Bolen et al, Journal of Fermentation and Bioengineering, vol. 69, pp. 211–214 (1990).
VanCauwenberge et al, Enzyme Microb. Technol., vol. 11, pp. 662–667 (Oct. 1989).
Bolen et al, Applied and Environmental Microbiology, vol. 52. pp. 660–664 (Oct. 1986).
Bolen et al, Biotechnology and Bioengineering Symp., 15, pp. 129–148 (1985).
Bolen et al, Biotechnology and Bioengineering, vol. XXVII, pp. 302–307 (1985).
Bolen et al, Annu. Meet. Am Soc. Microbiol. (1986)—Abstract only.
Smiley, et al, Biotechnol. Lett., vol. 4, pp. 601–610 (1982)—Abstract only.
Kotter et al, "Expression of the Pichia Stipitis . . . " Yeast 1990. vol. 6, Spec. Issue, S. S604, Jun.
Yang et al, "Purification and Properties of Xylitol", Applied Biochem. and Biotech. 1990, pp. 197–206.
Prior et al, "Fermentation of D–Xylose . . . ", Process Biochem. Feb., 1989, pp. 21–32.
Ho, et al, "Purification, Characterization, and . . . " Enzyme Microb. Technol., 1990, vol. 12, Jan., pp. 33–39.
Amore et al, "Fermentation of Xylose" Applied Microbiology and Biotechnology. 30: 351–357 (May 1989).
Rizzi et al, (I) "Purification and Kinetic Studies of XR from P. Stipitis", Applied Microbiology and Biotechnology. 29: 148–154 (1/88).
Rizzi et al. (II) "Purification and Properties of the NAD–Xylitol Dehydrogenase from P. Stipits" J. of Fermentation and Bioeng. 67: 20–24 (9/89).
Kotter et al, Curr, Genet., 18, 493–500 (1990).
Hagedorn et al. "Isolation and Characterization of xyl mutants." Current Genetics 16:27–33 (Jul. 1989).
Young et al. (1983) Science 222: 778–782.
McKnight (1983) PNAS 80:4412–4416.
Winnaker (1987) "From Genes to Clones"; Weinheim.
Hallborn et al. (1991) Bio/Technology 9:1090–1095.
Meinander et al (1994) Appl. Microbiol. Biotechnol. 42:334–339.
Koether et al (1993) Appl. Microbiol. Biotechnol. 38:776–783.
Beach et al. (1981) Nature 290:140–142.
Das et al. (1982) Current Genetics 6:123–128.
Sambrook et al (1989) Molecular Cloning; A Laboratory Manual, 2$^{nd}$ Ed., p. 8.46–8.53.

* cited by examiner

Primary Examiner—Elizabeth Slobodyansky
(74) Attorney, Agent, or Firm—Birch, Stewart, Kolasch & Birch, LLP

(57) ABSTRACT

This invention relates to recombinant-DNA-technology. Specifically this invention relates to new recombinant yeast strains transformed with xylose reductase and/or xylitol dehydrogenase enzyme genes. A yeast strain transformed with the xylose reductase gene is capable of reducing xylose to xylitol and consequently of producing xylitol in vivo. If both of these genes are transformed into a yeast strain, the resultant strain is capable of producing ethanol on xylose containing medium during fermentation. Further, the said new yeast strains are capable of expressing the said two enzymes. Xylose reductase produced by these strains can be used in an enzymatic process for the production of xylitol in vitro.

11 Claims, 10 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (iii) HYPOTHETICAL: NO (v) FRAGMENT TYPE: N-terminal (vi) ORIGINAL SOURCE:
      (A) ORGANISM: Pichia stipitis
      (B) STRAIN: CBS-6054

(ix) FEATURE:
      (A) NAME/KEY: Peptide
      (B) LOCATION: 1..9
      (D) OTHER INFORMATION: /label= peptide
          /note= "amino-terminal peptide from P.s. xylose
          reductase"

(x) PUBLICATION INFORMATION:
      (H) DOCUMENT NUMBER: FI 901771
      (I) FILING DATE: 06-APR-1990

(xi) SEQUENCE DESCRIPTION: SEQ ID NO:1:

Pro Xaa Ile Lys Leu Asn Ser Gly Tyr
1             5

(2) INFORMATION FOR SEQ ID NO:2:

(i) SEQUENCE CHARACTERISTICS:
      (A) LENGTH: 954 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (vi) ORIGINAL SOURCE:
     (A) ORGANISM: Pichia stipitis
     (B) STRAIN: CBS-6054

(ix) FEATURE:
     (A) NAME/KEY: CDS
     (B) LOCATION: 1..954
     (D) OTHER INFORMATION: /standard_name= "xylose reductase"

(x) PUBLICATION INFORMATION:
     (H) DOCUMENT NUMBER: FI 901771
     (I) FILING DATE: 06-APR-1990

(xi) SEQUENCE DESCRIPTION: SEQ ID NO:2:

```
ATG CCT TCT ATT AAG TTG AAC TCT GGT TAC GAC ATG CCA GCC GTC GGT       48
Met Pro Ser Ile Lys Leu Asn Ser Gly Tyr Asp Met Pro Ala Val Gly
 1               5                  10                  15

TTC GGC TGT TGG AAA GTC GAC GTC GAC ACC TGT TCT GAA CAG ATC TAC       96
Phe Gly Cys Trp Lys Val Asp Val Asp Thr Cys Ser Glu Gln Ile Tyr
                20                  25                  30

CGT GCT ATC AAG ACC GGT TAC AGA TTG TTC GAC GGT GCC GAA GAT TAC      144
Arg Ala Ile Lys Thr Gly Tyr Arg Leu Phe Asp Gly Ala Glu Asp Tyr
         35                  40                  45

GCC AAC GAA AAG TTA GTT GGT GCC GGT GTC AAG AAG GCC ATT GAC GAA      192
Ala Asn Glu Lys Leu Val Gly Ala Gly Val Lys Lys Ala Ile Asp Glu
 50                  55                  60

GGT ATC GTC AAG CGT GAA GAC TTG TTC CTT ACC TCC AAG TTG TGG AAC      240
Gly Ile Val Lys Arg Glu Asp Leu Phe Leu Thr Ser Lys Leu Trp Asn
 65                  70                  75                  80

AAC TAC CAC CAC CCA GAC AAC GTC GAA AAG GCC TTG AAC AGA ACC CTT      288
Asn Tyr His His Pro Asp Asn Val Glu Lys Ala Leu Asn Arg Thr Leu
                 85                  90                  95

TCT GAC TTG CAA GTT GAC TAC GTT GAC TTG TTC TTG ATC CAC TTC CCA      336
Ser Asp Leu Gln Val Asp Tyr Val Asp Leu Phe Leu Ile His Phe Pro
            100                 105                 110

GTC ACC TTC AAG TTC GTT CCA TTA GAA GAA AAG TAC CCA CCA GGA TTC      384
Val Thr Phe Lys Phe Val Pro Leu Glu Glu Lys Tyr Pro Pro Gly Phe
        115                 120                 125

TAC TGT GGT AAG GGT GAC AAC TTC GAC TAC GAA GAT GTT CCA ATT TTA      432
Tyr Cys Gly Lys Gly Asp Asn Phe Asp Tyr Glu Asp Val Pro Ile Leu
    130                 135                 140

GAG ACC TGG AAG GCT CTT GAA AAG TTG GTC AAG GCC GGT AAG ATC AGA      480
Glu Thr Trp Lys Ala Leu Glu Lys Leu Val Lys Ala Gly Lys Ile Arg
145                 150                 155                 160

TCT ATC GGT GTT TCT AAC TTC CCA GGT GCT TTG CTC TTG GAC TTG TTG      528
Ser Ile Gly Val Ser Asn Phe Pro Gly Ala Leu Leu Leu Asp Leu Leu
                165                 170                 175

AGA GGT GCT ACC ATC AAG CCA TCT GTC TTG CAA GTT GAA CAC CAC CCA      576
Arg Gly Ala Thr Ile Lys Pro Ser Val Leu Gln Val Glu His His Pro
            180                 185                 190

TAC TTG CAA CAA CCA AGA TTG ATC GAA TTC GCT CAA TCC CGT GGT ATT      624
Tyr Leu Gln Gln Pro Arg Leu Ile Glu Phe Ala Gln Ser Arg Gly Ile
        195                 200                 205

GCT GTC ACC GCT TAC TCT TCG TTC GGT CCT CAA TCT TTC GTT GAA TTG      672
Ala Val Thr Ala Tyr Ser Ser Phe Gly Pro Gln Ser Phe Val Glu Leu
    210                 215                 220

AAC CAA GGT AGA GCT TTG AAC ACT TCT CCA TTG TTC GAG AAC GAA ACT      720
Asn Gln Gly Arg Ala Leu Asn Thr Ser Pro Leu Phe Glu Asn Glu Thr
225                 230                 235                 240

ATC AAG GCT ATC GCT GCT AAG CAC GGT AAG TCT CCA GCT CAA GTC TTG      768
Ile Lys Ala Ile Ala Ala Lys His Gly Lys Ser Pro Ala Gln Val Leu
                245                 250                 255
```

```
TTG AGA TGG TCT TCC CAA AGA GGC ATT GCC ATC ATT CCA AAG TCC AAC    816
Leu Arg Trp Ser Ser Gln Arg Gly Ile Ala Ile Ile Pro Lys Ser Asn
            260                 265                 270

ACT GTC CCA AGA TTG TTG GAA AAC AAG GAC GTC AAC AGC TTC GAC TTG    864
Thr Val Pro Arg Leu Leu Glu Asn Lys Asp Val Asn Ser Phe Asp Leu
            275                 280                 285

GAC GAA CAA GAT TTC GCT GAC ATT GCC AAG TTG GAC ATC AAC TTG AGA    912
Asp Glu Gln Asp Phe Ala Asp Ile Ala Lys Leu Asp Ile Asn Leu Arg
            290                 295                 300

TTC AAC GAC CCA TGG GAC TGG GAC AAG ATT CCT ATC TTC GTC            954
Phe Asn Asp Pro Trp Asp Trp Asp Lys Ile Pro Ile Phe Val
305                 310                 315

(2) INFORMATION FOR SEQ ID NO:3:

(i) SEQUENCE CHARACTERISTICS:
        (A) LENGTH: 318 amino acids
        (B) TYPE: amino acid
        (D) TOPOLOGY: linear (ii) MOLECULE TYPE: protein (xi) SEQUENCE DESCRIPTION: SEQ ID NO:3:

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
                20                  25                  30

Arg Ala Ile Lys Thr Gly Tyr Arg Leu Phe Asp Gly Ala Glu Asp Tyr
            35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270
```

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
        290                 295                 300

Phe Asn Asp Pro Trp Asp Trp Asp Lys Ile Pro Ile Phe Val
305                 310                 315

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: -
        (B) LOCATION: 1..40
        (D) OTHER INFORMATION: /label= oligonucleotide
            /note= "upstream primer for PCR amplification of
            P.s. xylose reductase"

(x) PUBLICATION INFORMATION:
        (H) DOCUMENT NUMBER: FI 901771
        (I) FILING DATE: 06-APR-1990

(xi) SEQUENCE DESCRIPTION: SEQ ID NO:4:

GCGGATCCTC TAGAATGCCT TCTATTAAGT TGAACTCTGG                          40

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: YES (ix) FEATURE:
        (A) NAME/KEY: -
        (B) LOCATION: 1..40
        (D) OTHER INFORMATION: /label= oligonucleotide
            /note= "downstream primer for PCR amplification of
            P.s. xylose reductase"

(x) PUBLICATION INFORMATION:
        (H) DOCUMENT NUMBER: FI 901771
        (I) FILING DATE: 06-APR-1990

(xi) SEQUENCE DESCRIPTION: SEQ ID NO:5:

TTGGATCCTC TAGATTAGAC GAAGATAGGA ATCTTGTCCC                          40

(2) INFORMATION FOR SEQ ID NO:6:

(i) SEQUENCE CHARACTERISTICS:
        (A) LENGTH: 696 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
             (A) ORGANISM: Pichia stipitis
             (B) STRAIN: CBS-6054

(ix) FEATURE:
             (A) NAME/KEY: CDS
             (B) LOCATION: 1..693
             (D) OTHER INFORMATION: /standard_name= "xylitol
                 dehydrogenase"

(x) PUBLICATION INFORMATION:
             (H) DOCUMENT NUMBER: FI 901771
             (I) FILING DATE: 06-APR-1990

(xi) SEQUENCE DESCRIPTION: SEQ ID NO:6:

```
ATG AAC TTG GAA AGA ACC AAG TCC GCT GCC AAA GAA GTT TTG GGC TGG        48
Met Asn Leu Glu Arg Thr Lys Ser Ala Ala Lys Glu Val Leu Gly Trp
 1               5                  10                  15

GGT GAA GAG ACG TTG AAG GGT GAA CAC GCT TCA GCC ATC GGC CAA GTT        96
Gly Glu Glu Thr Leu Lys Gly Glu His Ala Ser Ala Ile Gly Gln Val
             20                  25                  30

TCC GCC TGG TCC TGC AAC ATT GGG GAT GCT GAG GCA GTA GAC GCT ACT       144
Ser Ala Trp Ser Cys Asn Ile Gly Asp Ala Glu Ala Val Asp Ala Thr
         35                  40                  45

TTC AGC TCC ATC AAC GAA CAC CAC GGC AAG ATC GCT GAC TTG TTG ATT       192
Phe Ser Ser Ile Asn Glu His His Gly Lys Ile Ala Asp Leu Leu Ile
     50                  55                  60

AAC ACC GCT GGA TAC TGT GAA AAC TTC CCT GCC GAA ACG TAC CCG GCT       240
Asn Thr Ala Gly Tyr Cys Glu Asn Phe Pro Ala Glu Thr Tyr Pro Ala
 65                  70                  75                  80

ACT AAC GCT GAA AGC ATC ATG AAG GTG AAC GGT TTG GGC TCA TTC TAC       288
Thr Asn Ala Glu Ser Ile Met Lys Val Asn Gly Leu Gly Ser Phe Tyr
                 85                  90                  95

GTT TCG CAA TCG TTC GCT AGA CCA TTG ATC CAG AAC AAC TTG AGA GGC       336
Val Ser Gln Ser Phe Ala Arg Pro Leu Ile Gln Asn Asn Leu Arg Gly
            100                 105                 110

TCT ATC ATC TTG ATT GGC TCA ATG TCT GGA ACA ATT GTC AAC GAC CCA       384
Ser Ile Ile Leu Ile Gly Ser Met Ser Gly Thr Ile Val Asn Asp Pro
        115                 120                 125

CAA CCC CAA TGT ATG TAC AAC ATG TCC AAG GCT GGA GTG ATC CAC TTG       432
Gln Pro Gln Cys Met Tyr Asn Met Ser Lys Ala Gly Val Ile His Leu
    130                 135                 140

GTC AGA TCG TTG GCC TGC GAA TGG GCC AAG TAC AAC ATC AGA GTC AAC       480
Val Arg Ser Leu Ala Cys Glu Trp Ala Lys Tyr Asn Ile Arg Val Asn
145                 150                 155                 160

ACC TTA TCA CCA GGC TAT ATT TTG ACT CCT TTA ACC AGA AAC GTG ATT       528
Thr Leu Ser Pro Gly Tyr Ile Leu Thr Pro Leu Thr Arg Asn Val Ile
                165                 170                 175

TCT GGC CAC ACA GAG ATG AAG GAA GCC TGG GAA TCC AAG ATC CCC ATG       576
Ser Gly His Thr Glu Met Lys Glu Ala Trp Glu Ser Lys Ile Pro Met
            180                 185                 190

AAG AGA ATG GCC GAA CCC AAG GAA TTC GTG GGG TCC ATC TTA TAC TTG       624
Lys Arg Met Ala Glu Pro Lys Glu Phe Val Gly Ser Ile Leu Tyr Leu
        195                 200                 205

GCA AGC GAG ACT GCT TCT TCC TAC ACT ACG GGC CAC AAT TTG GTT GTG       672
Ala Ser Glu Thr Ala Ser Ser Tyr Thr Thr Gly His Asn Leu Val Val
    210                 215                 220

GAC GGA GGA TAT GAA TGC TGG TAG                                       696
Asp Gly Gly Tyr Glu Cys Trp
225                 230
```

(2) INFORMATION FOR SEQ ID NO:7:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO:7:

```
Met Asn Leu Glu Arg Thr Lys Ser Ala Ala Lys Glu Val Leu Gly Trp
 1               5                  10                  15

Gly Glu Glu Thr Leu Lys Gly Glu His Ala Ser Ala Ile Gly Gln Val
                20                  25                  30

Ser Ala Trp Ser Cys Asn Ile Gly Asp Ala Glu Ala Val Asp Ala Thr
            35                  40                  45

Phe Ser Ser Ile Asn Glu His His Gly Lys Ile Ala Asp Leu Leu Ile
        50                  55                  60

Asn Thr Ala Gly Tyr Cys Glu Asn Phe Pro Ala Glu Thr Tyr Pro Ala
 65                  70                  75                  80

Thr Asn Ala Glu Ser Ile Met Lys Val Asn Gly Leu Gly Ser Phe Tyr
                85                  90                  95

Val Ser Gln Ser Phe Ala Arg Pro Leu Ile Gln Asn Asn Leu Arg Gly
               100                 105                 110

Ser Ile Ile Leu Ile Gly Ser Met Ser Gly Thr Ile Val Asn Asp Pro
           115                 120                 125

Gln Pro Gln Cys Met Tyr Asn Met Ser Lys Ala Gly Val Ile His Leu
       130                 135                 140

Val Arg Ser Leu Ala Cys Glu Trp Ala Lys Tyr Asn Ile Arg Val Asn
145                 150                 155                 160

Thr Leu Ser Pro Gly Tyr Ile Leu Thr Pro Leu Thr Arg Asn Val Ile
                165                 170                 175

Ser Gly His Thr Glu Met Lys Gly Ala Trp Glu Ser Lys Ile Pro Met
            180                 185                 190

Lys Arg Met Ala Glu Pro Lys Glu Phe Val Gly Ser Ile Leu Tyr Leu
        195                 200                 205

Ala Ser Glu Thr Ala Ser Ser Tyr Thr Thr Gly His Asn Leu Val Val
    210                 215                 220

Asp Gly Gly Tyr Glu Cys Trp
225                 230
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: -
        (B) LOCATION: 1..24
        (D) OTHER INFORMATION: /label= oligonucleotide
           /note= "Lambda gt11-specific primer for PCR
           amplification of insert DNA"

```
    (x) PUBLICATION INFORMATION:
        (H) DOCUMENT NUMBER: FI 901771
        (I) FILING DATE: 06-APR-1990

(xi) SEQUENCE DESCRIPTION: SEQ ID NO:8:

GGTGGCGACG ACTCCTGGAG CCCG                                              24

(2) INFORMATION FOR SEQ ID NO:9:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (iv) ANTI-SENSE: NO (ix) FEATURE:
         (A) NAME/KEY: -
         (B) LOCATION: 1..24
         (D) OTHER INFORMATION: /label= oligonucleotide
             /note= "Lambda-gt11 specific primer for
             amplification of insert DNA"

(x) PUBLICATION INFORMATION:
         (H) DOCUMENT NUMBER: FI 901771
         (I) FILING DATE: 06-APR-1990

(xi) SEQUENCE DESCRIPTION: SEQ ID NO:9:

TTGACACCAG ACCAACTGGT AATG                                              24
```

PRODUCTION OF ETHANOL FROM XYLOSE

This application is a Divisional Application of application Ser. No 08/336,198, filed on Nov. 3, 1994, now U.S. Pat. No. 5,866,382 which in turn is a Continuation Application of Ser. No. 07/848,694 filed on Mar. 9, 1992 and now abandoned, which in turn is a Continuation-In-Part Application of Ser. No. 07/527,775, filed on May 24, 1990 now abandoned. This application is also a continuation-in-part of PCT International Application No. PCT/FI91/00103 which has an international filing date of Apr. 8, 1991 which designated the United States. The entire contents of each of these applications are hereby incorporated by reference.

FIELD OF THE INVENTION

This invention relates to recombinant-DNA-technology. Specifically this invention relates to new recombinant yeast strains transformed with xylose reductase and/or xylitol dehydrogenase enzyme genes. A yeast strain transformed with the xylose reductase gene is capable of reducing xylose to xylitol and consequently of producing xylitol in vivo. If both of these genes are transformed into a yeast strain, the resultant strain is capable of producing ethanol on xylose containing medium during fermentation.

Further, the said new yeast strains are capable of expressing the said two enzymes. Xylose reductase produced by these strains can be used in an enzymatic process for the production of xylitol in vitro.

BACKGROUND OF THE INVENTION

Xylose Utilization

Xylose appears in great abundance in nature. It can constitute as much as 40% of a lignocellulosic material (Ladisch et al., 1983). By fermentation xylose can be converted to ethanol which can be used as a liquid fuel or a chemical feedstock. Enzymatically or as a by-product of fermentation xylose can also be converted to xylitol which is a promising natural- sweetener having dental caries reducing properties. Xylitol can also be used by diabetics. For the production of ethanol which is a cheap product it is important that the raw material can be fermented directly with as little pretreatment as possible. For the production of xylitol which is meant for human consumption it is important that the process involves GRAS organisms.

Natural xylose utilizers are found among bacteria, yeast and fungi. In all organisms xylose is converted to xylulose which is phosphorylated to xylulose-5-phosphate (X5P) with xylulokinase. X5P then enters the Embden-Meyerhof pathway (glycolysis) via the pentose phosphate shunt.

Bacteria like *Escherichia coli*, Bacillus sp., Streptomyces sp. and Actinoplanes sp. convert xylose directly to xylulose with a xylose isomerase (XI). Thus bacteria do not produce xylitol as an intermediate during xylose utilization. Those which ferment xylose to ethanol do so with poor yields because a number of by-products are also produced (Skoog and Hahn-Hägerdal, 1988). In xylose utilizing yeasts such as *Pichia stipitis, Candida shehatae* and *Pachysolen tannophilus* this reaction occurs in two steps: first xylose is reduced to xylitol with a xylose reductase (XR) and the xylitol is oxidized with a xylitol dehydrogenase (XDH) to xylulose.

Pure xylose solutions are fermented with high yields and good productivities by xylose utilizing yeasts such as *P. stipitis, C. shehatae* and *P. tannophilus* (Slininger et al., 1987; Prior et al., 1989). However, they do not generally survive in the hostile environment of an untreated raw material such as eg. spent sulphite liquor or hydrogen fluoride-pretreated and acid-hydrolyzed wheat straw (Lindén and Hahn-Hägerdal, 1989). The one exception, *P. tannophilus,* produces mainly xylitol and glycerol in response to this environment. In order to efficiently ferment such raw materials with the xylose utilizing yeasts such as *P. stipitis, C. shehatae* and *P. tannophilus* the raw material has to undergo expensive pretreatments with ion-exchange resins (Clark and Mackie, 1984) or steam stripping (Yu et al., 1987).

*Saccharomyces cerevisiae,* bakers' yeast, ferments spent sulphite liquor or hydrogen fluoride-pretreated and acid-hydrolyzed wheat straw to ethanol (Lindén and Hahn-Hägerdal, 1989). *S. cerevisiae* cannot utilize xylose efficiently and cannot grow on xylose as a sole carbon source. In the presence of the bacterial enzyme xylose isomerase, which converts xylose to xylulose, *S. cerevisiae* can, however, ferment both pure xylose solutions (Hahn-Hägerdal et al., 1986) and untreated raw materials (Lindén and Hahn-Hägerdal, 1989a,b) to ethanol with yields and productivities that are in the same order of magnitude as those obtained in hexose fermentations.

Similar results have been obtained with *Schizosaccharomyces pombe* (Lastick et al., 1989). Thus, both *S. cerevisiae* and *Sch. pombe* have a functioing xylulokinase enzyme. It has also been found that *S. cerevisiae* can take up xylose (Batt et al., 1986; van Zyl et al., 1989; Senac and Hahn-Hägerdal, 1990).

Gong (1985) discloses a process for obtaining ethanol directly from D-xylose by xylose fermenting yeast mutants. According to Gong a parent yeast strain is selected (e.g. Candida sp. or *Saccharomyces cerevisiae*), which originally may have the ability to utilize D-xylose, and this parent strain is then exposed e.g. to UV-radiation so as to induce mutation. However, no information about the reason why the mutants obtained are able to utilize xylose, is given in the reference. Further, Gong did not introduce any new coding and/or regulatory sequences to said strains by genetic engineering techniques to enhance xylose fermentation.

Xylitol is industrially manufactured at the moment by chemical reduction of hemi-cellulose hydrolysates. Poisoning of the expensive catalyst used in the reduction step and formation of side-products difficult to be separated from the end product are the main problems in this process.

In literature there are numerous examples of microbiological methods to produce xylitol from pure xylose (eg. Onishi and Suzuki, 1966; Barbosa et al., 1988). Best producers in this method are yeasts especially belonging to the Candida-genera. Also some bacteria such as Enterobacter (Yoshitake et al., 1973a) and Corynebacterium species (Yoshitake et al., 1973b) and some molds eg. *Penicillium chrysogenum* (Chiang and Knight, 1960) produce xylitol from pure xylose.

In a microbiological method describing the best yields of xylitol production (Ojamo et al., 1987) *Candida guilliermondii* yeast is cultivated under strictly controlled aeration in a xylose containing medium either as a batch or a fed-batch process. Xylitol yields 50–65% were obtained. The yield could be increased to 76% by adding furfuraldehyde to the cultivation medium.

Cell-free extracts from *Candida pelliculosa* (xylose reductase) and Methanobacterium sp. (hydrogenase, $F_{420}$, NADP, $F_{420}$/(NADP oxidoreductase) has been used to produce xylitol in a membrane reactor with 90% conversion (Kitpreechavanich, 1985). With a cell-free extract from a Corynebacterium species 69% conversion has been obtained when 6-phosphogluconate was used for regeneration of the cofactor.

It has been shown that glucose dehydrogenase from *B. megaterium* has suitable properties as a NADPH regenerating enzyme (Kulbe et al., 1987). Thus gluconic acid from glucose can be produced simultaneously with xylitol in the enzymatic process. For the retention of the enzymes and the cofactor one can use ultrafiltration membranes. Cofactor retention may be achieved by the use of a derivatized cofactor having high enough molecular weight for the retention (Kulbe et al., 1987) or better by using negatively charged ultrafiltration membranes (Kulbe et al., 1989).

Attraction to use an enzymatic method is based on the possibility to use impure xylose containing raw materials which in the microbiological methods would inhibit the metabolism of the microbe used. Also the yields of xylitol are higher than in the microbiological methods with natural strains. On the other hand any microbiological method is more simple in large-scale practice at the moment.

The natural xylose utilizing yeasts such as *P. stipitis*, Candida sp. and *P. tannophilus* are not suitable for the production of either ethanol or xylitol for several reasons. The fermentation to ethanol requires pretreatment of the raw material which is cost-prohibitive for a cheap end-product such as ethanol. These species also lack the GRAS-status. Thus xylose utilization would most suitably be based on the use of baker's yeast which has a GRAS-status.

In order to make *S. cerevisiae* an efficient xylose utilizer for the production of xylitol and ethanol an efficient enzyme system for the conversion of xylose to xylitol and xylulose should be introduced into this yeast. For the production of ethanol from xylose the XI genes from *E. coli* (Sarthy et al., 1987), *B. subtilis* and *Actinoplanes missouriensis* (Amore et al., 1989) have been cloned and transformed into *S. cerevisiae*. The XI protein made in *S. cerevisiae* had very low (1/1000 of the enzyme produced in bacteria) or no enzymatic activity. Thus, for some reasons the bacterial enzyme can not be made functional in yeast. Another possibility would be to transfer into *S. cerevisiae* the genes encoding XR and XDH from another yeast. The enzymes of *P. stipitis* should be good candidates in the light of the efficient utilization of pure xylose solutions discussed above. It can be anticipated that enzymes from another yeast would function better than bacterial enzymes when expressed in yeast. In addition, xylitol and ethanol could be produced with the same system and the system would combine the good xylose utilization of *P. stipitis* with resistance to inhibitors and general acceptance of *S. cerevisiae*.

SUMMARY OF THE INVENTION

The present invention describes the isolation of genes coding for xylose reductase (XR) and xylitol dehydrogenase (XDH) from certain yeasts having these genes, the characterization of the genes and their transfer into, and their expression in *Saccharomyces cerevisiae*.

This invention thus provides new recombinant yeast strains expressing xylose reductase and/or xylitol dehydrogenase enzymes.

The yeast strains according to the invention being transformed with the XR gene are capable of reducing xylose to xylitol in vivo. Xylose reductase produced by the new yeast strains according to the invention is also used in an enzymatic process for the production of xylitol in vitro.

The present invention further provides new yeast strains transformed with both of the above mentioned two genes. The coexpression of these genes renders the strain capable of fermenting xylose to ethanol from pure xylose solution or xylose containing solutions such as lignocellulosic hydrolyzates.

DETAILED DESCRIPTION OF THE INVENTION

Figure 1A:
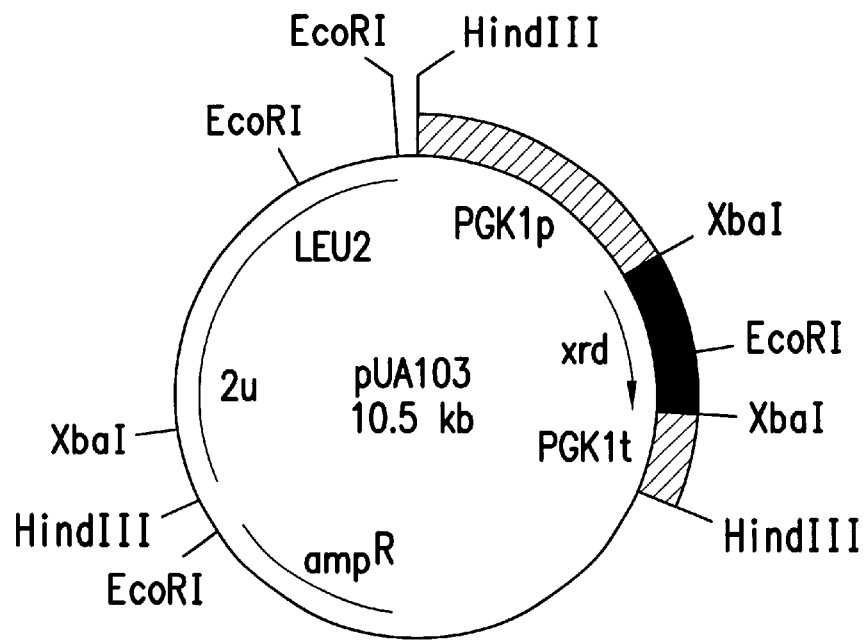
FIGS. 1A and 1B show the xylose reductase gene integrated into pMA91 and pRS305 resulting in plasmids pUA103 (FIG. 1A) and pUA107 (FIG. 1B) respectively.

Xylose reductase (xrd) and xylitol dehydrogenase (xdh) genes to be used in this invention are isolated from an organism containing these genes, eg. *Pichia stipitis*. Also other suitable yeasts and other fungi, such as *Pachysolen tannophilus*, Kluyveromyces spp., *Petromyces albertensis* and Candida spp. can be used. It is to be noted that also enzymes from other organisms, for instance the so called aldose reductases such as the rat lens aldose reductase, show significant xylose reductase activity (Old et al., 1990) and could be used for the purpose of this invention.

The yeast to be transformed with these genes can be any suitable yeast, for xylitol production preferably having the GRAS-status, eg. any *Saccharomyces cerevisiae* yeast strain, (eg. DBY746, AH22, S150-2B, GPY55-15Bα, VTT-A-63015, VTT-A-85068, VTT-C-79093), any Kluyveromyces sp. or *Schizosaccharomyces pombe*. Transfer of the genes into these yeasts can be achieved, for instance, by using the conventional methods described for these organisms. It is to be noticed that, if wanted, also Pichia itself can be transformed with these genes in order to obtain increased or modulated expression of the genes. *Saccharomyces cerevisiae* strains are preferable for the purposes of this invention.

The DNA sequence coding for XR enzyme is isolated from *P. stipitis* by conventional methods. In the preferred embodiment, cDNA is synthesized from mRNA and cloned into λ gt11 vector. Using immuno screening with XR specific antibodies, the positive clone is isolated and subcloned into BS+ vector for sequencing. Gene encoding XR of *P. stipitis* can be cloned also by expression in *S. cerevisiae* because it, does not contain any introns. Another possibility is the use of oligonucleotides, designed on the basis of the amino acid sequence of the enzyme, in hybridization of a gene bank.

To construct a plasmid suitable for transformation into a yeast, the gene coding for XR is cloned into a suitable yeast expression vector, such as pMA91 (Mellor et al., 1983), comprising the appropriate yeast regulatory regions. These regulatory regions can be obtained from yeast genes such as the PGK1, ADH1, GAL1, GAL10, CUP1, GAP, CYC1, PHO5, for instance. Alternatively, also the regulatory regions of the Pichia gene encoding XR can be used to express the gene in *S. cerevisiae*. The plasmid carrying the xrd gene encoding XR is capable of replicating autonomously when transformed into the recipient yeast strain. The gene encoding XR together with the appropriate yeast regulatory regions can also be cloned into a single copy yeast vector such as pRS305 (Sikorski and Hieter, 1989).

Alternatively, the gene coding for XR can also be integrated into the yeast chromosome, into the ribosomal RNA locus, for instance. For this purpose the ribosomal sequences of a suitable plasmid, eg. plasmid pIRL9 are released, and cloned appropriately to BS+ vector. The gene coding for XR, coupled in between suitable yeast promoter and terminator regions, is released from the hybrid vector comprising the gene and cloned into the plasmid obtained at the previous stage. From this resulting plasmid the expression cassette, flanked by ribosomal sequences can be released. This fragment is cotransformed into a yeast with an autonomously replicating plasmid carrying a suitable marker for transformation. The plasmid can be later on removed from the cells containing the xrd gene integrated in the chromosome by cultivating the cells in non-selective conditions. This way, recombinant strains can be obtained which carry no extra foreign DNA such as bacterial vector sequences. If a polyploid yeast strain, such as VTT-A-63015, is used the gene can be integrated also to an essential locus such as the PGK1 or the ADH1 locus.

An object of this invention is thus to provide the specific xylose reductase gene. The sequence of the xrd gene can be determined from the plasmids carrying it by using eg. the double stranded dideoxy nucleotide sequencing method (Zagursky et al., 1986). The sequence of the xrd gene encoding XR of *P. stipitis* is given as the SEQ ID NO. 2.

Another object of this invention is to provide specific yeast vectors comprising the xrd gene. Such a vector is either an autonomously replicating multicopy or a single copy plasmid or a vector capable of integrating into the yeast chromosome, as described above.

Still another object of this invention is to provide yeast strains which comprise the DNA sequence coding for XR and are capable of expressing this enzyme.

Thus a process for producing xylose reductase enzyme is also provided. This process comprises:
(a) isolating the DNA sequence coding for xylose reductase from a suitable donor organism;
(b) constructing a yeast vector carrying said DNA sequence;
(c) transforming the vector obtained into a suitable yeast host to obtain a recombinant host strain;
(d) cultivating said recombinant host strain under conditions permitting expression of said xylose reductase; and
(e) recovering said xylose reductase.

Enzymes from organisms having a GRAS status are preferred in an enzymatic production of xylitol. Xylose reductase from *Pichia stipitis* have excellent enzymatical properties such as kinetic constants and stability without special stabilizing agents such as thiol-protecting chemicals. Production of this enzyme is now possible in a yeast having a GRAS status. The transformed yeast cells are cultivated in an appropriate medium. As the cultivation medium, a cheap medium such as one based on molasses can be used as xylose is not needed for induction as in naturally xylose utilizing yeasts. Yeast with intracellular xylose reductase is produced with a good yield in a fed-batch process.

The yeast is concentrated and washed by eg. centrifugation and xylose reductase is liberated into the solution by cell disruption methods such as high pressure homogenization or glass bead milling. After clarification of the homogenate by filtration or centrifugation xylose reductase is further purified by chromatographic methods.

For the production of xylitol in vitro a crude homogenate or purified xylose reductase is used in an enzyme reactor together with a cofactor (NAD/NADH or NADP/NADPH) and a cofactor regenerating enzyme such as glucose dehydrogenase, formate dehydrogenase or any other enzyme having good enough stability, requirements for environmental conditions coping with those of xylose reductase and suitable kinetic properties (Bückmann, 1979; Wandrey et al., 1981; 1982; Kulbe et al., 1989). The enzymes and the cofactor are typically kept in the reactor system by ultrafiltration membranes especially those with a negative charge. The cofactors may also be coimmobilized with the cofactor regenerating enzymes (Reslow et al., 1988). The reaction mixture is pumped through the reactor and the substrates and the products are filtered through the membrane. The products can be separated from the substrates by eg. chromatographic or crystallization methods and the substrates can be recycled to the reaction mixture.

Further, this invention provides a microbiological process for producing xylitol which process comprises:
(a) cultivating a recombinant yeast strain carrying a DNA sequence coding for xylose reductase enzyme in xylose containing medium; and
(b) recovering the xylitol formed in the medium.

In a microbiological xylitol production with a recombinant yeast the in vivo regeneration of the cofactor NADPH or NADH must be secured in one way or another. With a yeast construction having only xylose reductase and not xylitol dehydrogenase gene, cofactor regeneration can be achieved by adding a co-carbon-substrate such as glucose, glycerol, ribose or ethanol. With such a system, 95–100% yield of xylitol from xylose can be obtained. In this system with *S. cerevisiae,* xylitol is not metabolized further and consequently higher yields of xylitol can be obtained than with natural xylitol producing organisms. When the yeast has also xylitol dehydrogenase gene (see hereunder) cofactor regeneration may happen through a slight flow of xylitol further in the metabolism. This flow can be controlled by relative amounts of expression of the enzymes xylose reductase and xylitol dehydrogenase or by controlling the metabolism of the yeast by oxygen transfer rate or by adding enzyme inhibitors such as iodoacetate to the cultivation medium.

In the preferred embodiment, for the isolation of the xdh gene of *P. stipitis* a chromosomal gene bank is first made into *E. coli* in a cosmid p3030 (Penttilä, et al., 1984) or in another yeast vector, and recombinant plasmids are isolated and transformed into yeast. The xdh gene can be found by its expression in yeast, which can be detected by an activity plate assay. A cDNA copy for this gene can be isolated similarly by an activity plate assay from a λ gt11 cDNA expression library made in *E. coli*.

An alternative method for the isolation of the xdh gene from *P. stipitis* is to purify XDH from a donor yeast by chromatographic methods and determine the N-terminal amino acid sequence thereof. A mixture of oligonucleotides based on the obtained N-terminal amino acid sequence of XDH protein can be designed. This oligonucleotide mixture can then be used in hybridization of a gene bank, or together with an oligo-dT-primer to amplify by PCR reaction xdh specific sequences from a mRNA population. The resulting gene or cDNA is cloned into BS+ vector, or a similar vector, and the sequence of the xdh gene is then obtained by conventional methods.

It is thus also an object of this invention to provide a specific xylitol dehydrogenase gene (SEQ ID NO. 6).

The xdh gene can be expressed in yeast from the chromosomal copy cloned into for instance the yeast cosmid p3030 (Penttilä et al., 1984). To such a yeast carrying the xdh gene, the plasmid carrying the xrd gene can be transformed.

Also, the full length xdh cDNA can be cloned into a suitable expression vector, such as pMA91 or pKB102 (Blomqvist et al., 1991) in between appropriate yeast regulatory regions, preferably using the yeast PGK1 or ADH1 promoter and terminator. The expression cassette built into pKB102 can be released from the resulting plasmid and cloned into an autonomously replicating yeast multicopy vector or into a single copy yeast vector, which carry a suitable marker, eg. URA3 or HIS3 for yeast transformation. These resulting plasmids can then be transformed into a suitable host strain or into the strains carrying the gene encoding XR.

In addition, it is shown that other genes coding for XDH activity, such as the XYL2 gene of *P. stipitis* (Kötter et al., 1990), when expressed from *S. cerevisiae* promoter sequences, can result in high level XDH activity in *S. cerevisiae*.

The xdh gene can also be integrated into the yeast genome in the same manner as described above for the xrd gene.

Thus, a further object of this invention is to provide a method for constructing new yeast strains capable of expressing xylose reductase or xylitol dehydrogenase or coexpressing xylose reductase and xylitol dehydrogenase, which method comprises:
 (a) isolating the DNA sequences coding for xylose reductase and xylitol dehydrogenase from a suitable donor organism;
 (b) constructing a yeast vector carrying either of the said DNA sequences; and
 (c) transforming either of the vectors obtained or both of them into a suitable yeast host.

The present invention thus provides a process for coexpressing active xylose reductase and xylitol dehydrogenase in a yeast strain, which process comprises:
 (a) isolating the DNA sequences coding for xylose reductase and xylitol dehydrogenase from a suitable donor organism;
 (b) constructing yeast vectors each carrying one of said DNA sequences;
 (c) transforming the vectors obtained to a suitable host to obtain a recombinant yeast strain;
 (d) cultivating said recombinant yeast strain in a xylose containing medium; and
 (e) isolating and purifying the products (ethanol, xylitol, acetic acid) formed in the medium.

The recombinant yeast strains according to this invention coexpressing xylose reductase and xylitol dehydrogenase enzymes are potent ethanol producers from xylose by fermenting the xylose containing fraction in for instance lignocellulosic hydrolyzates such as by-products from the forest products industry, eg. spent sulphite liquor, or in raw materials which have been obtained by pretreatment to make the xylose fraction available for fermentation by treatment at elevated temperatures in the presence or absence of chemicals such as sulphur dioxide and in combination with acid or enzymatic hydrolysis. The consumption of xylose and the formation of products (ethanol, xylitol, acetic acid etc.) are analysed for instance by HPLC (Hahn-Hägerdal et al., 1986; Lindén and Hahn-Hägerdal, 1989a, b).

EXAMPLE 1

Purification of Xylose Reductase from *Pichia stipitis*

*P. stipitis* was grown in a 1 litre fermentor in xylose containing medium (0.3% yeast extract, 0.3% malt extract, 0.5% peptone, 1.9% $KH_2PO_4$, 0.3% $(NH_4)_2H-PO_4$, 0.1% $MgSO_4$ and 5% xylose, pH 5) and harvested in late logarithmic growth phase. 30 g wet weight of cell paste was disrupted using freeze pressing (X-press) and centrifuged 1500 g, 10 min to get a cell free extract.

The crude extract was concentrated 2-fold and applied to a Sephadex G-200 (Pharmacia, Uppsala, Sweden) column (137 ml). At a flow rate of 6 ml/h the proteins were eluted and fractions (9 ml) containing XR activity were pooled.

The pooled fraction was applied to a DEAE-Sepharose (Pharmacia) column (37 ml) equilibrated with 0.02M ammonium phosphate buffer pH 6.0 and eluted with a 250 ml gradient of 0–0.5 M NaCl in 0.02 M ammonium phosphate buffer at a flow rate of 12 ml/min. Fractions containing XR activity were pooled (6 ml) and concentrated to 1 ml. 1 ml of the concentrated sample was applied to a 1 ml HPLAC column (cibacron blue F36-A; Perstorp Biolytica, Lund, Sweden) equilibrated with 0.02 M ammonium phosphate buffer pH 6.0. Elution of XR was performed with a 0–2 M NaCl gradient in ammonium phosphate buffer at a flow rate of 1 ml/min. Fractions containing XR activity were pooled (6 ml) and dialysed over night at 4° C.

Figure 6:
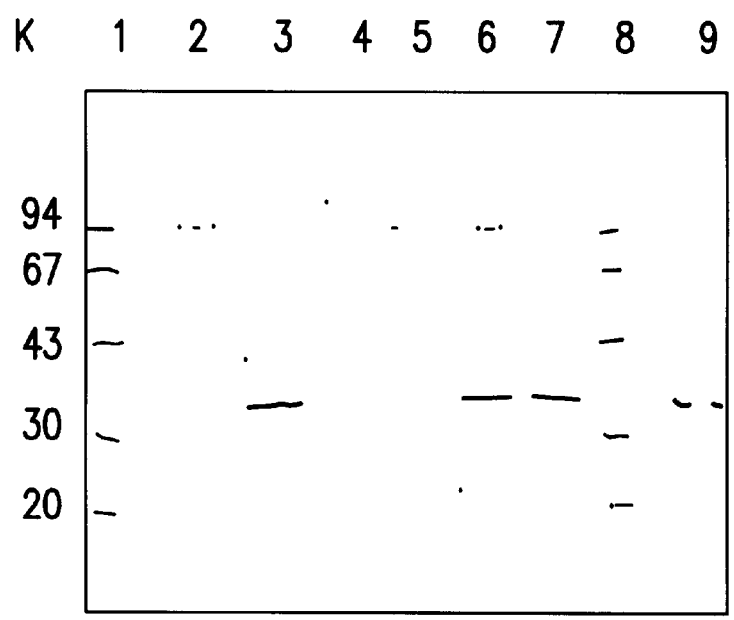
FIG. 6 shows Western analysis of XR produced in *S. cerevisiae* from the following plasmids and from *P. stipitis*. Lanes: 1 molecular weight standars (LMW, Pharmacia); 2 pRS305; 3 pUA107; 4 empty lane; 5 pMA91; 6 pUA103; 7 purified XR enzyme; 8 LMW; 9 *Pichia stipitis*. Samples were taken from French pressed cell lysates for lanes 2, 3, 5, 6 and 9.

Purity and molecular weight was determined by gradient SDS-polyacrylamide gel (T 8.8–21.3%, C 2.6%) electrophoresis (Laemmli, 1970) and native gradient polyacrylamide gel (Pharmacia premade gel, 4/30) electrophoresis (Pharmacia vertical electrophoresis system). Low and high molecular weight standards from Pharmacia were used. Staining of gel was performed with 0.1% Coomassie Blue R-250 (Sigma) in 25% methanol and 10% acetic acid. In SDS-PAGE and in native-PAGE gel the XR fraction after HPLAC appeared as a single band (data not shown). Specific staining of XR with the zymogram technique showed that the single band in the native-PAGE gel was XR (data not shown). Molecular weight estimation with SDS-PAGE (see FIG. 6) and native-PAGE showed a molecular weight of 38000±1000 for the subunits and 76000±1000 for the native protein.

The purified enzyme was used to produce polyclonal antibodies and to make a N-terminal amino acid sequence of the enzyme (Marc Bauman at Dept. of Medical Chemistry, Univ. of Helsinki) (SEQ ID NO. 1).

EXAMPLE 2

Cloning of the Gene Coding for XR from *Pichia stipitis*

1 litre of *P. stipitis* culture was grown in xylose containing medium (see example 1) and harvested in late log phase. Harvested cells were converted to sphearoplasts with Zymolyase, suspended into 60 ml of GuSCN solution and RNA was isolated according to Chirgwin et al. (1979). RNA was then run through an oligo(dT) cellulose affinity chromatography column. Poly (A+)mRNA was eluted by decreasing the ionic strength of the elution buffer. cDNA was synthesized from mRNA using the cDNA synthesis kit of Amersham and cloned into the λ gt11 vector using the Amersham cDNA cloning kit. After 3–4 h growth, the plaques were replica plated onto nitrocellulose membranes soaked in IPTG, and incubated over night. The membranes were then used for immuno screening of transformants (Young and Davies, 1983) using rabbit antiserum against XR and goat anti rabbit antibodies coupled with alkaline phosphatase. Positive clones were picked from the plates and the insert DNA was amplified with PCR (Güssow and Clackson, 1989) using vector specific primers. The DNA fragments obtained were used for restriction enzyme analysis and for further cloning after BamHI cleavage into BamHI cleaved BS+ (Stratagene) vector. The longest cDNA clone pJHXR20 was sequenced using the double stranded dideoxy nucleotide method (Zagursky et al., 1986).

Verification of the cloning of the full length cDNA coding for XR was obtained by comparing the N-terminal amino acid sequence of the protein with the sequenced gene (SEQ ID NO. 1, SEQ ID NO. 3)

Figure 1B:
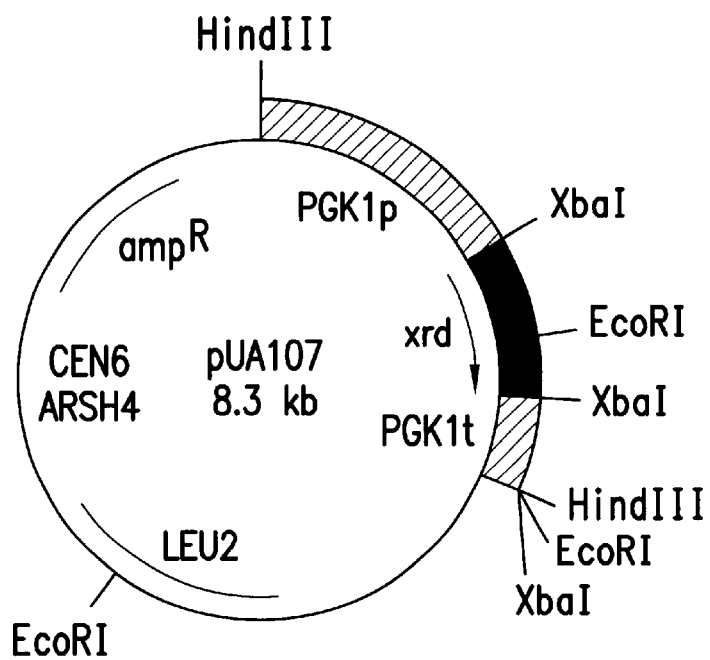

The chromosomal copy of the xrd gene was obtained by PCR reaction of total chromosomal DNA isolated (Cryer et al., 1979) from *P. stipitis* CBS-6054 (Prior et al., 1989) using primers corresponding to the 5' (GCGGATCCTCTAGAATGCCTTCTATTAAGTTG AACTCTGG) (SEQ ID NO. 4) and to the 3' MTGGATC-CTCRAGATTAGACGAAGATAGGAA TCTTGTCCC) (SEQ ID NO. 5) end of the coding region and carrying BamHI and XbaI restriction sites. The PCR product was digested with BamHI and cloned into plasmid pMA91 (Mellor et al., 1983) at the BglII site to obtain plasmid pUA103 (FIG. 1). The DNA sequence of the chromosomal copy was compared to that of the cDNA in plasmid pJHXR20, and was shown to contain no introns.

EXAMPLE 3
Purification of XDH from *Pichia stipitis*

*Pichia stipitis* was grown in xylose containing medium as described (example 1). 30 g wet weight of cell paste was disrupted using freeze pressing (X-press) and centrifuged 1500 g 10 min. The centrifuged cellfree extract was concentrated 3 times and 5 ml was gel filtrated at a flow rate of 6 ml/h through a 137 ml Sepharose 6B column equilibrated with 0.05 M ammonium phosphate buffer pH 6, 25% glycerol, 1 mM DTT, 1 mM EDTA. Fractions containing XDH activity measured according to Smiley and Bolen (1982) were pooled and applied on a 37 ml ion exchange chromatography column (DEAE-sepharose) equilibrated with 0.05 M ammonium phosphate buffer pH 6, 25% glycerol, 1 mM DTT, 1 mM EDTA. XDH fractions were eluted with a 250 ml salt gradient of 0–0.5 M NaCl at a flow rate of 12 ml/min and pooled. The partially purified enzyme was run in a polyacrylamide gel and blotted onto a PVD membrane. The band corresponding to XDH was cut out and the N-terminal amino acid sequence was determined directly from the membrane.

EXAMPLE 4
Cloning of the Gene Coding for XDH and Expression in *S. cerevisiae*

Figure 2:
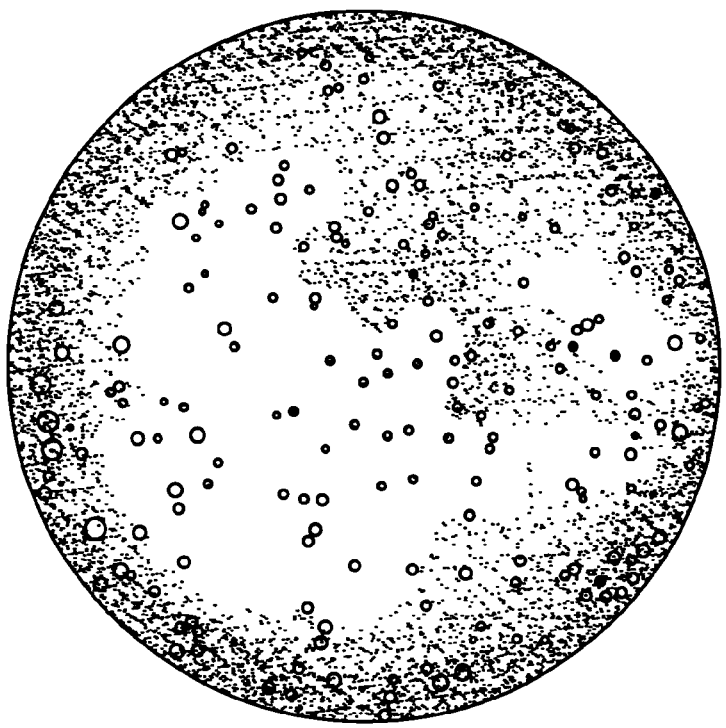
FIG. 2 Activity plate assay of a XDH positive λ gt11 clone
Figure 3:
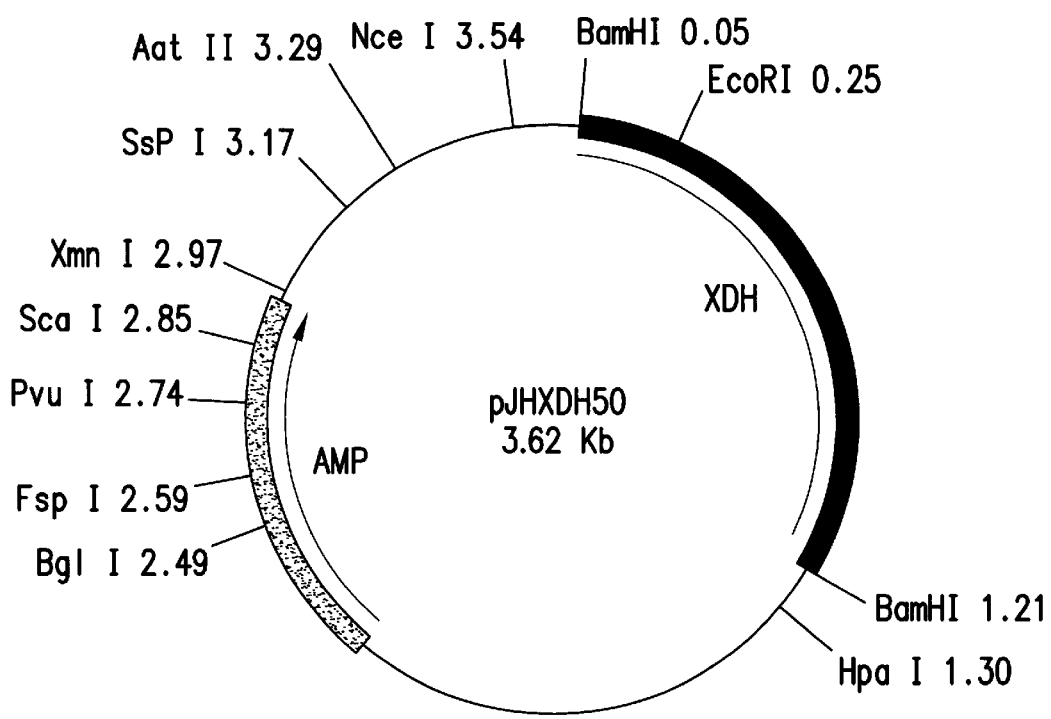
FIG. 3 shows the picture of the plasmid pJHXDH50 carrying the xdh gene.

The same λ gt11 cDNA library as obtained and described in Example 2 was plated and replica plated onto nitrocellulose membrane soaked in IPTG and incubated for 3 hours. The membranes were then used for specific XDH activity (zymogram) screening by soaking the membranes in 10 ml of zymogram solution (0.1 M phosphate buffer pH 7.0, 1.5 mM NAD, 0.25 mM nitroblue tetrazolium, 65 μM phenazine methosulphate, 0.4 M xylitol). Positive clones (FIG. 2) were picked from the plates and the insert DNA of two of the clones was amplified with PCR (Güssow and Clackson, 1989) using vector specific primers (5'-GGTGGCGACGACTCCTGGAGCCCG (SEQ ID NO. 8) 5'-TTGACACCAGACCAACTGGTAATG (SEQ ID NO. 9). The DNA fragments obtained were of the same size and were used for restriction enzyme analysis to check non-cutting and cutting enzymes and for further cloning after BamHI cleavage into Bamfi cleaved pSP72 vector (Promega). The plasmid pJHXDH50 carries the longest cDNA clone (FIG. 3). Sequencing of the xdh cDNA was carried out (SEQ ID NO. 6).

Figure 4:
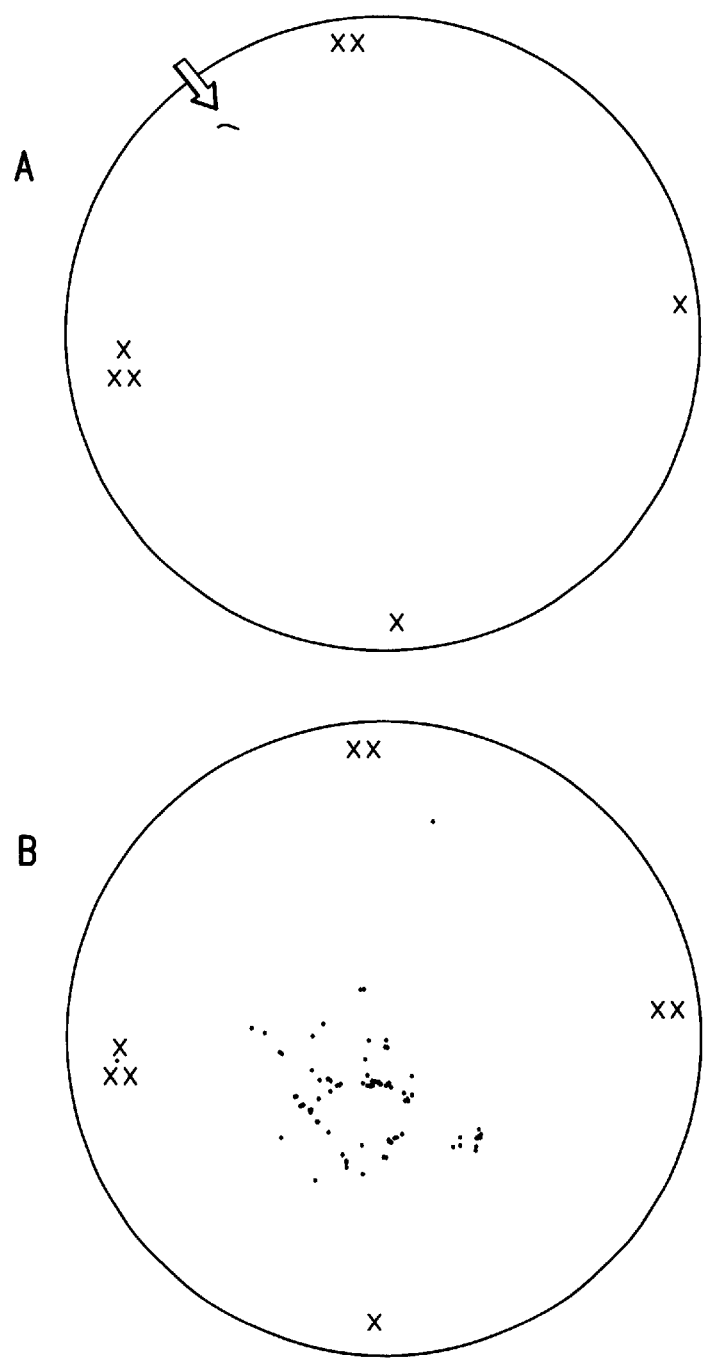
FIGS. 4A and 4B show a plate activity assay of a recombinant *S. cerevisiae* strain VTT-C-91181 producing XDH, on the original transformation plate (FIG. 4A) and as single colonies obtained from this transformant (FIG. 4B).

To clone the chromosomal copy of the xdh gene, chromosomal DNA was isolated (Cryer et al., 1979) from *P. stipitis* strain CBS-6054 (Prior et al., 1989) and cut partially with Sau 3A. Fragments of 35–45 kb in size were purified by fractionating the partially digested DNA in a sucrose gradient (15%–40%), and the fragments were ligated to a p3030 yeast cosmid vector (Penttilä et al., 1984), cut with BamHI. The ligated molecules were packaged into λ particles using the in vitro packaging kit of Amersham Ltd. (UK) and transfected into *E. coli* HB101 (Maniatis et al., 1982). Recombinant cosmid DNA was isolated from about 15000 pooled gene bank clones obtained and transformed into a *S. cerevisiae* strain S150-2B (a, his3-del1, leu2-3, leu2-112, trpl-289, ura3-52, cir⁺, Gal⁺) (Baldari et al., 1987) by selecting for His⁺ transformants on Sc-his plates. The gene bank was replica plated onto nitrocellulose filters, the cells were broken by incubating the filters for 5 min. in chloroform and the activity assay was performed as described above for the λ gt11 library. Several positive clones were obtained (strains H494, H495, H496, H497 and VTT-C-91181), and the strain VTT-C-91181 (FIG. 4) was used for further studies. The presence of xdh sequences in this clone was verified by colony hybridization (Rose et al., 1990) using as a probe a PCR fragment made from the cDNA clone.

XDH activity of the strain VTT-C-91181 was tested according to Smiley and Bolen (1982) from French pressed total cell lysate containing 25% glycerol. DNA from VTT-C-91181 was isolated and the plasmid pMW22 rescued by transformation of the DNA into *E. coli* DH5α. The xdh sequence on this plasmid was confirmed by conventional methods.

Figure 9:
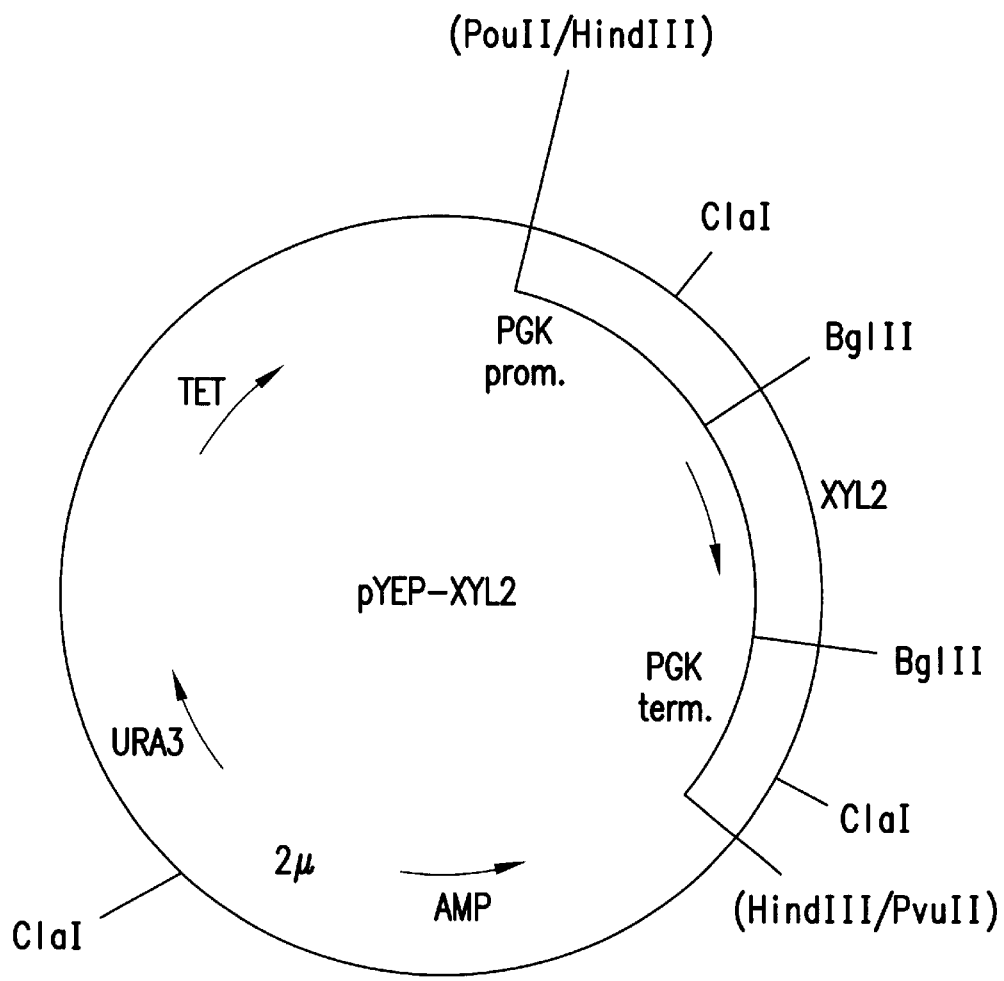
FIG. 9 shows the plasmid pYEP-XYL2 carrying the XYL2 gene under the PGK promoter.

Also another *P. stipitis* gene XYL2, reported to encode XDH activity (Kötter et al., 1990) was cloned from total *P. stipitis* DNA (Cryer et al.,1979) by PCR using primers specific for the 5' and 3' end of the coding region and carrying BglII restriction enzyme sites at the ends. The PCR fragment was digested with BglII and cloned at the BglII site of pMA91 (Mellor et al., 1983) to obtain plasmid pP-XYL2. pP-XXYL2 was transformed into *S. cerevisiae* strain S150-2B by selecting for Leu+ colonies and the transformant stored for further study was designated H547. From pP-XYL2 the expression cassette was released with HindIII and filled in with Klenow and cloned at the PvuII site of YEp24 (Rose et al., 1990) to obtain plasmid pYEP-XYL2 (FIG. 9).

The *S. cerevisiae* strain VTT-C-91181 carrying the plasmid pMW22 was deposited according to the Budapest Treaty with the accession No. NCYC 2352 at the National Collection of Yeast Cultures (NCYC), UK, on Mar. 29, 1991.

EXAMPLE 5
Expression of XR in *S. cerevisiae*

The gene coding for XR, with the regulatory regions of the PGK gene, was released from the plasmid pUA103 (Example 2) with HindIII and cloned at the HindIII site of the single copy vector pRS305 (Sikorski and Hieter, 1989). The resulting plasmid pUA107 (FIG. 1), in which the XR encoding gene was in the right orientation towards the yeast PGK promoter, was transformed using the LiCl method (Ito et al., 1983), and selecting for Leu+ transformants, into *S. cerevisiae* strains S150-2B (see Example 4) and GPY55-15Bα (leu2-3, leu2-112, ura3-52, trpl-289, his4-519, prb1, cir+) giving the new recombinant strains *S. cerevisiae* H481 and *S. cerevisiae* H479, respectively. The plasmid pUA103 transformed into the strains S150-2B and GPY-15Bα resulted in strains H477 and H475, respectively.

Cultures of the yeast strains H475 and H477 have been deposited under the terms and conditions of the Budapest Treaty at the Deutsche Sammlung Von Mikroorganismen and Zellculturen GmbH, Mascheroder Weg 1b, D-38124 Braunschweig, Germany, on May 16, 1997, under the accession numbers DSM 11546 and DSM 11547, respectively.

Figure 5:
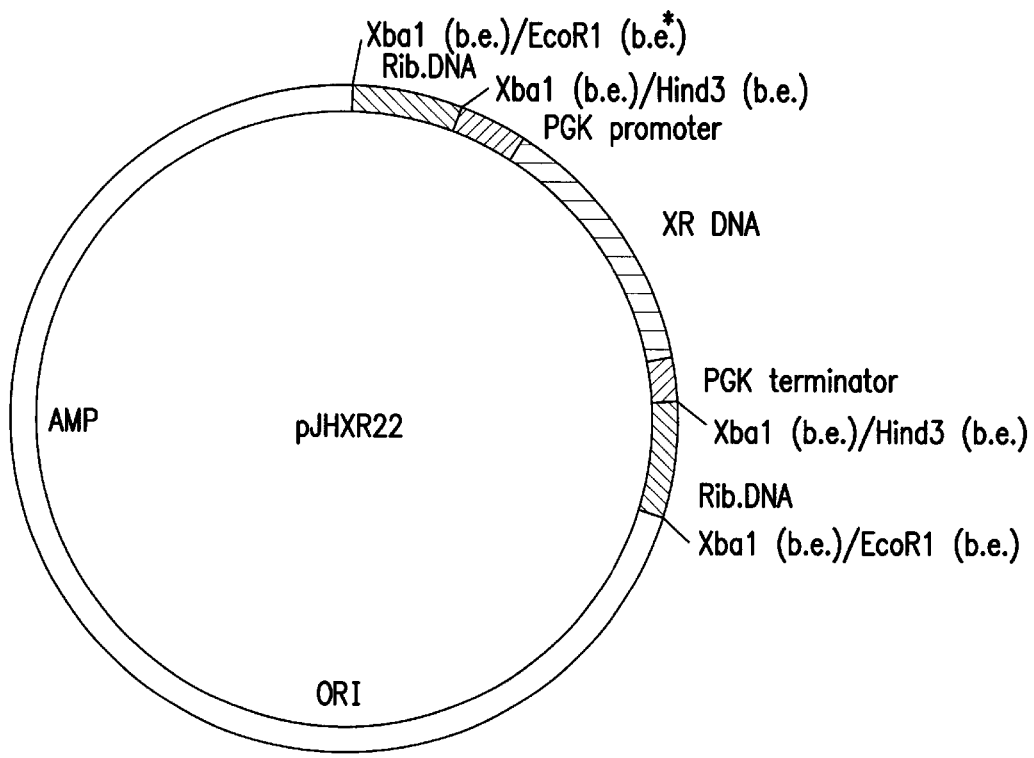
FIG. 5 shows the xylose reductase expression cassette flanked by ribosomal sequences integrated into BS+, generating the vector pJHXR22.

The gene coding for XR was also integrated into the yeast chromosome into the ribosomal RNA loci. The ribosomal sequences of plasmid pIRL9 were released with EcoRI, blunt-ended and cloned at the blunt-ended XbaI site of BS+ to obtain vector pJHR21. The gene coding for XR, coupled in between the PGK promoter and terminator was released from the vector pUA103 as a HindIII fragment, blunt-ended and cloned at the blunt-ended XbaI site in the ribosomal sequences of the plasmid pJHR21. From this resulting plasmid pJHXR22 (FIG. 5), the expression cassette, flanked by ribosomal sequences, was released by cutting in the unique restriction sites of the BS+ polylinker. This fragment was cotransformed into yeast with an autonomously replicating plasmid carrying a marker for transformation. The transformants obtained were screened for the presence of the gene coding for XR by enzyme activity tests as described above and the integration pattern was checked by Southern analysis. The autonomously replicating plasmid was removed from the cells carrying the XR expression cassette by cultivating the cells in non-selective YPD growth medium.

Figure 7A:
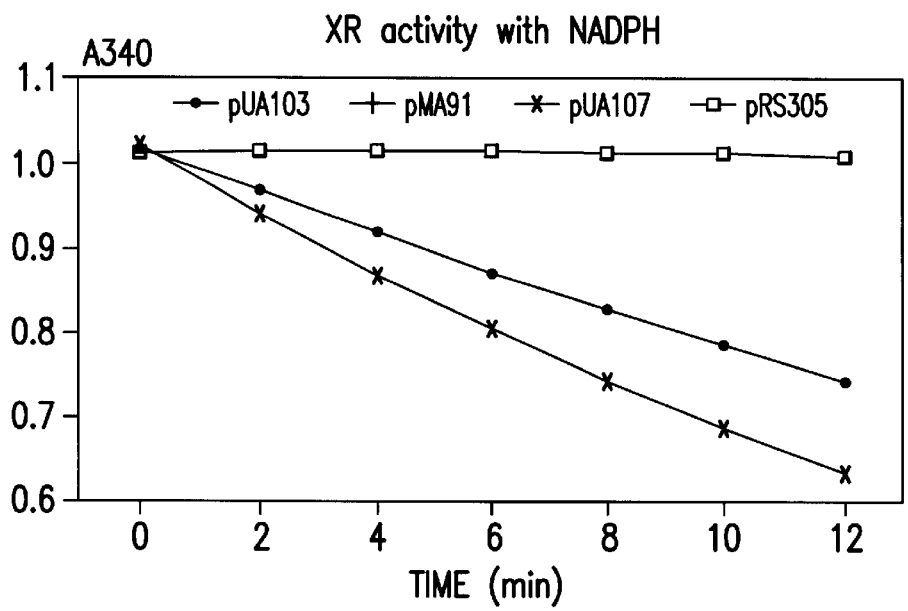
FIGS. 7A and 7B show XR activity of *S. cerevisiae* strains transformed with pUA103 and pUA107 using as a cofactor either NADH (FIG. 7A) or NADPH (FIG. 7B), and of the control strains carrying the vector pRS305 or pMA91.
Figure 7B:
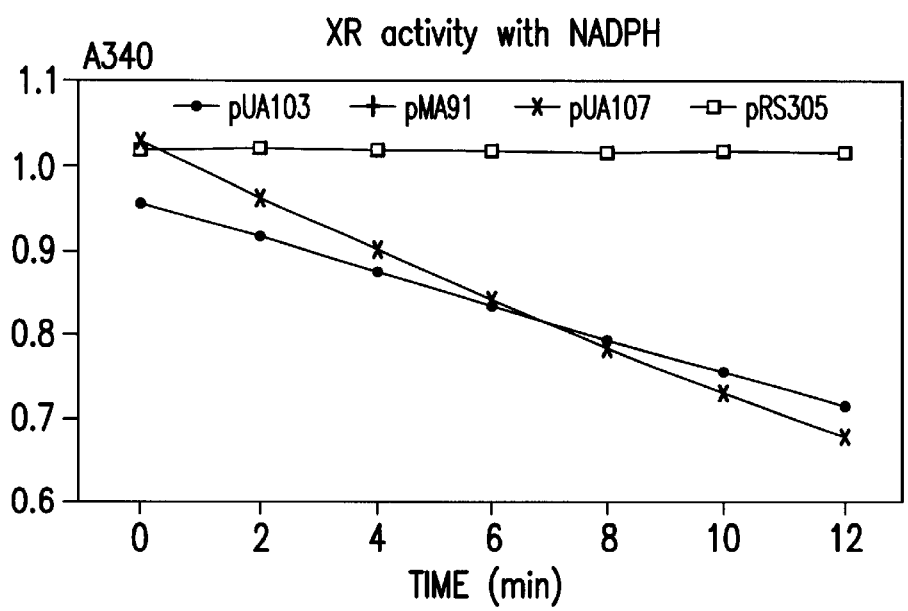

The transformants were grown in minimal selective medium and the expression of XR was analyzed by Western blotting using XR specific antibody and the alkaline phosphatase method of Promega (FIG. 6), and by enzyme activity measurements (Smiley and Bolen, 1982) from crude extracts of yeast cells broken by French press (FIG. 7).

EXAMPLE 6
Purification of XR from Recombinant *S. cerevisiae*

A recombinant *S. cerevisiae* strain H477 was cultivated in a 1.5 l fermentor in a Sc-leu medium containing 20 g/l glucose. Growth was followed by turbidity measurements and the cells were collected at late exponential growth phase by centrifugation, washed and resuspended in 0.1 M phosphate buffer pH 7.0 containing 1.5 mM phenyl methyl sulfonyl fluoride, to a yeast concentration of 100 g dry weight/l. Cells were disrupted with 3 passes at 1000 bar through a high pressure homogenizer (French-press). The homogenate was partially clarified by 30 min centrifugation at 15000 g. XR was purified from the clarified homogenate as described for *P. stipitis* in example 1.

EXAMPLE 7
Production of Xylitol in vitro

A reaction mixture containing 0.33 M xylose, 0.33 M glucose-6-phosphate, 0.67 mM NADPH, 0.1 M phosphate buffer (pH 7.0), 1 nkat/ml XR activity of purified XR (Example 6) or from a diluted crude homogenate of the strain H475, and 1 nkat/ml glucose-6-phosphate dehydrogenase was incubated at 20° C. for 5 h. Samples were withdrawn intermittently and analysed for xylitol using a xylitol kit from Boehringer. A constant xylitol production rate exceeding 0.14 g $h^{-1}l^{-1}$ was observed.

EXAMPLE 8
Co-expression of XR and XDH

Figure 10:
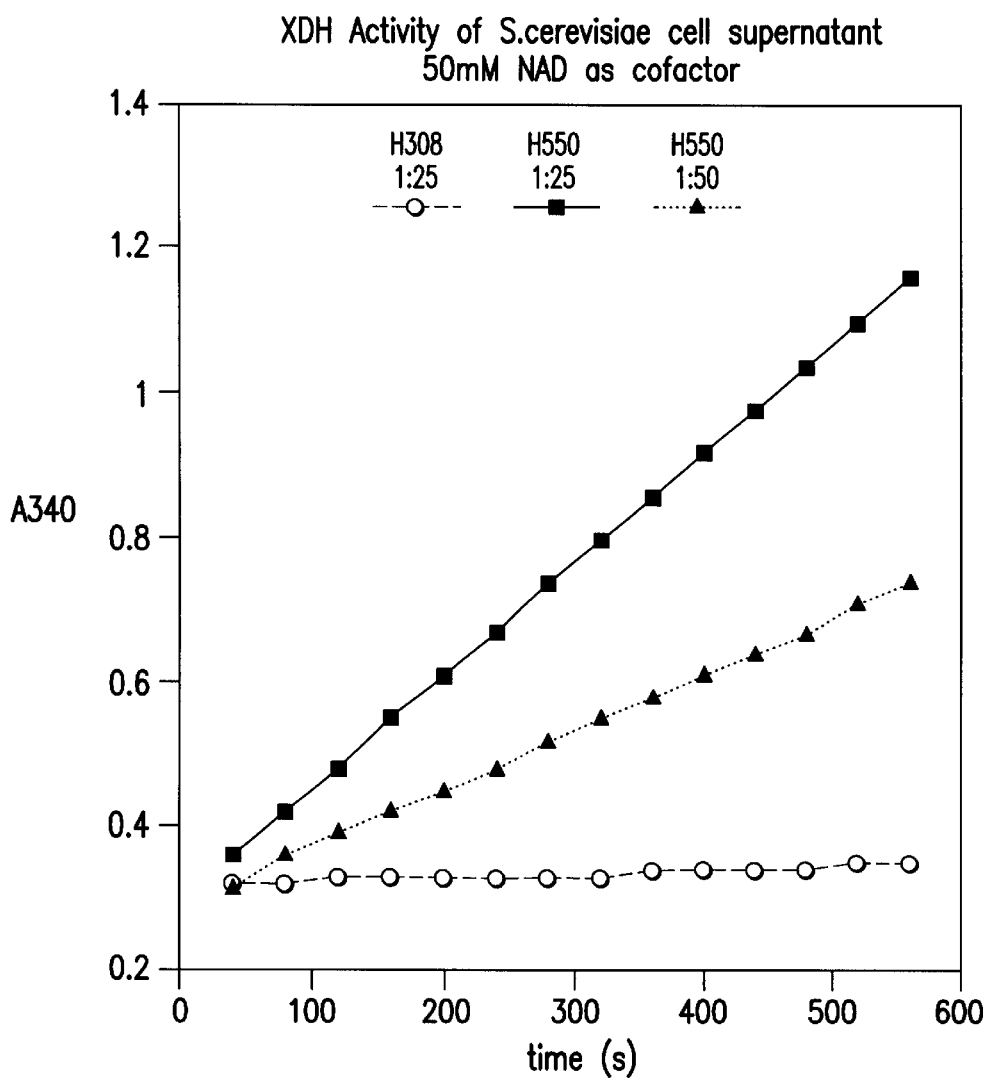
FIG. 10 shows XDH activity of the *S. cerevisiae* strain H550 using two dilutions (1:25, 1:50) of the crude cell extract. H308 is the untransformed control strain S150-2B.

The plasmids pUA103 and pUA107 were trasformed into the strain VTF-C-91181 which carries the xdh gene on the plasmid pMW22. Transformants were selected, and also later kept, on Sc-leu-his-plates. The retainment of XDH activity was confirmed by a plate activity assay and the XR activity by enzyme activity measurement as described above (FIG. 10). The two clones studied further, carrying the plasmids pUA103 and pMW22, were named H492 and H493.

Plasmid pYEP-XYL2 carrying the XYL2 gene (Example 4) was transformed into the strain H477 (Example 5) carrying the plasmid pUA103 by selecting for Leu+Ura+ transformants. A transformant carrying both pUA103 and pYEP-XYL2 was designated H550. The XDH activity of H550 was tested as described above (FIG. 10).

A culture of the yeast strain H550 was deposited under the terms and conditions of the Budapest Treaty at the Deutsche Sammlung Von Mikroorganismen und Zeliculturen GmbH, Mascheroder Weg 1b, D-38124 Braunschweig, Germany, on May 16, 1997, under the accession number DSM 11548.

Figure 8:
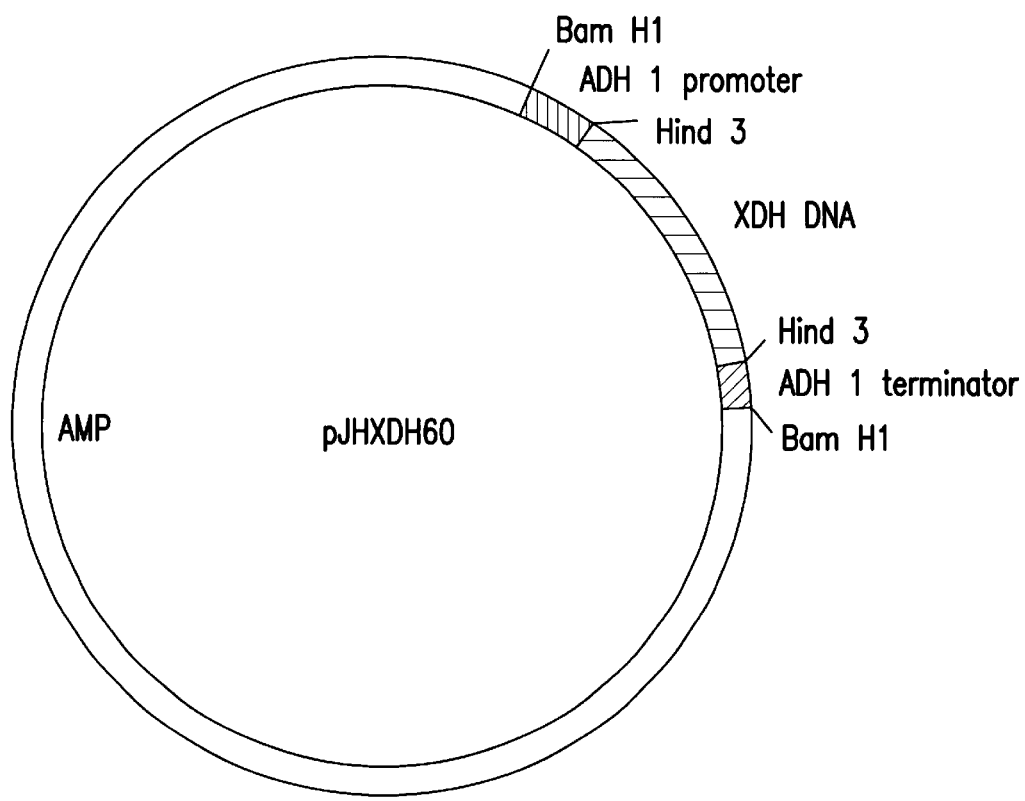
FIG. 8 shows the xylitol dehydrogenase gene integrated into pKB102 generating plasmid pJHXDH60.

The coding region of the xdh gene was isolated by PCR and cloned at the HindIII site in the vector pKB102 (Blomqvist et al. 1991) in between the yeast ADH1 promoter and terminator. The expression cassette was released with BamHI from the resulting plasmid pJHXDH60 (FIG. 8) and cloned into the autonomously replicating yeast vector p3030 at the BamHI site generating the plasmid pJ XDH70. The resulting plasmid was transformed into the strain H477 carrying the gene encoding XR (Example 5) selecting the transformants on Sc-leu-his-plates. The expression of the xdh gene in *S. cerevisiae* was tested by enzyme activity measurement (Smiley and Bolen, 1982). The transformant studied further was designated Y550.

EXAMPLE 9
Production of Xylitol in vivo by Recombinant *S. cerevisiae*

The yeast strains H475 and H477 were cultivated in a 1.5 l fermentor in a medium containing 10 g/l yeast extract, 20 g/l bacto-peptone and 20 g/l glucose. Cultivation temperature was 30° C. pH was controlled between 4.5 and 8.0. Agitation speed was 400 rpm and aeration rate 0.5 vvm. When glucose was consumed according to the analysis of the samples from the broth, a feed of a solution containing 1 g glucose and 19 g xylose in 100 ml was started at a rate of 0.09 ml/min. After 83 hours of total cultivation time, xylitol concentration in the broth was 12.5 g/l as analysed by HPLC. Thus over 95% yield of xylitol from xylose fed to the culture was achieved. By using the control strain carrying the vector pMA91 less than 8% of the xylose was consumed in an analogous experiment.

EXAMPLE 10
Xylose Fermentation by Recombinant *S. cerevisiae*

*S. cerevisiae* strains H550 and Y550 described in example 8 were cultivated on a rotary shaker in Sc-Leu-Ura or Sc-Leu-His medium, respectively, containing 4 g/l glucose and 20 g/l xylose. Rotating speed was 100 rpm. The consumption of xylose and the formation of xylitol were followed during fermentation by taking samples and analysing them by HPLC (Hahn-Hägerdal et al., 1986; Linden and Hahn-Hägerdal, 1989a, b) and ethanol was measured with the enzymatic kit of Boehringer. In repeated experiments comparable amounts of ethanol were obtained with both strains, with a mean value of 6.3 g/l in 18 h cultivation time, resulting in mean productivity of 0.35 g/l/h. In these conditions a non-transformed control strain produces theoretically 2 g/l of ethanol from the glucose added and in practice well below 2 g/l.

EXAMPLE 11
Fermentation of Xylose Containing Raw Materials with Recombinant *S. cerevisiae*

*S. cerevisiae* strains H550 and Y550 were cultivated as in example 10 in a fermentation medium, where xylose was replaced by spent sulphite liquor. Xylose was converted to cells, ethanol and xylitol.

REFERENCES

Amore, R., Wilhelm, M. and Hollenberg, C. P. (1989) Appl. Microbiol. Biotechnol. 30: 351–357.

Baldari, C., Murray, J. A. H., Ghiara, P., Cesarcni, G., and Galotti, C. L. (1987) EMBO J. 6: 229–234.

Barbosa, M. F. S., de Medeira, M. B., de Mancilha, I. M., Schneider, H. and Lee, H. 1988. Screening of yeasts for production of xylitol from D-xylose and some factors which affect xylitol yield in *Candida guilliermondii*. J. Ind. Microbiol. 3, 241–251.

Batt, C. A., Carvallo, S., Easson, D. D., Akedo, M. and Sinskey, A. J. 1986. Metabolic pathway in *Saccharomyces cerevisiae*. Biotechnology and Bioengineering 28, 549–553.

Bergmeyer, H. U., Gruber, W. and Gutmann, I. (1974) in Methods of Enzymatic Analysis (Bergmeyer, H. U., ed.) 2nd ed., vol. 3, pp. 1323–1330, Verlag Chemie, Weinheim and Academic Press, Inc., New York, London.

Blomqvist, K., Suihko, M.-L., Knowles, J. and Penttilä, M. (1991) Chromosomal integration and expression of two bacterial α-acetolactate decarboxylase genes in brewer's yeast. Appl. Environ. Microbiol. 57, 2796–2803.

Bückmann, A. F. (1979) German Patent No 28.41.414.

Chiang, C. and Knight, S. G. 1960. Metabolism of D-xylose by moulds. Nature 188, No. 4744, 79–81.

Chirgwin, J. M., Przybyla, A. E., MacDonald, R. J. and Rutter, W. J. (1979) Isolation of biologically active ribonucleic acid from sources enriched in ribonuclease. Biochemistry 18: 5294–5299.

Clark, T. A. and Mackie, K. L. (1984) J. Chem. Tech. Biotechnol. 34b: 101–110.

Cryer, D. R., Eccleshall, R. and Marmur, J. (1975) Isolation of yeast DNA. Methods Cell Biol. 12: 39–44.

Gong, C.-S. (1985). U.S. Pat. No. 4,511,656.

Güissow, D. and Clackson, T. (1989) Direct clone characterization from plaques and colonies by the polymerase chain reaction. Nucl. Acids Res. 17: 4000-.

Hahn-Hägerdal, B., Berner, S. and Skoog, K. 1986. Improved ethanol production from xylose with glucose isomerase and *Saccharomyces cerevisiae* using the respiratory inhibitor azide. Appl. Microbiol. Biotechnol. 24, 287–293.

Ito, H., Fukuda, Y., Murata, K. and Kimura, A. (1983) Transformation of intact yeast cells treated with alkali cations. J. Bact. 153: 163–168.

Kitpreechavanich, V., Nishio, N., Hayashi, M. and Nagai, S. 1985. Regeneration & retention of NADP(H) for xylitol production in an ionized membrane reactor. Biotechnol. Lett. 7, 657–662.

Kulbe, K. D., Schwab, U. and Gudernatsch, W. 1987. Enzyme-catalyzed production of mannitol and gluconic acid. Ann. N.Y. Acad. Sci. 506, 552–568.

Kulbe, K. D., Howaldt, M. W., Schmidt, K., Röthig, T. R. and Shmiel, H. 1989. Rejection and continuous regenreation of native coenzymes NAD(H)/NADP(H) in a charged ultrafiltration membrane enzyme reactor. Poster at the 10th Enzyme Engineering Conference, Sep. 24–29 1989, Kashikojima, Japan.

Kötter, P., Amore, R., Hollenberg, C. P. and Ciriacy, M. 1990. Isolation and characterization of the *Pichia stipitis* xylitol dehydrogenase gene, XYL2, and construction of a xylose-utilizing *Saccharomyces cerevisiae* transformant. Curr. Genet. 18, 497–500.

Ladisch, M. R., Lin, K. W., Voloch, M. and Tsao, G. T. (1983) Enzyme Microb. Technol. 5: 82–102.

Laemmli, U. K. (1970) Cleavage of structural proteins during the assembly of the head of bacteriophage T4. Nature 227: 680–685.

Lastick, S. M., Tucker, M. Y., Beyette, J. R., Noll, G. R. and grohman, K. (1989) Appl. Microbiol. Biotechnol. 30: 574–579.

Lindén, T. and Hahn-Hägerdal, B. (1989a) Enzyme Microb. Technol. 11: 583–589.

Lindén, T. and Hahn-Hägerdal, B. (1989b) Biotechnol. Techniques 3: 189–192.

Maniatis, T., Fritsch, E. F. and Sambrook, J. (1982). Molecular cloning. A laboratory manual. Cold Spring Harbor Laboratory, New York.

Mellor, J., Dobson, M. J., Roberts, N. A., Tuite, M. F., Emtage, J. S., White, S., Lowe, P. A., Patel, T., Kingsman, A. J. and Kingsman, S. M. (1983) Efficient synthesis of enzymatically active calf chymosin in *Saccharomyces cerevisiae*. Gene 24: 1–14.

Ojamo, H., Ylinen, L. and Linko, M. (1987) Finnish Patent 76377.

Old, S. E., Sato, S., Kador, P. F. and Carper, D. A. 1990. In vitro expression of rat lens aldose reductase in *Escherichia coli*. Proc. Natl. Acad. Sci. 87, 4942–4945.

Onishi, H. and Suzuki, T. (1966) The production of xylitol, L-arabinitol and ribitol by yeasts. Agr. Biol. Chem. 30: 1139–1144.

Penttilä, M. E., Nevalainen, K. M. H., Raynal, A. and Knowles, J. K. C. 1984. Mol. Gen. Genet. 194: 494–499.

Prior, B. A., Kilian, S. G. and du Preez (1989) Process Biochemistry 2: 21–32.

Reslow, M., Adlercreutz, Mattiasson, B. (1988) Eur. J. Biochem. 177: 313–318.

Rose, M. D., Winston, F. and Hieter, P. 1990. Methods in yeast genetics. Cold Spring Harbor Laboratory Press, 1990.

Sarthy, A. V., McConaughy, B. L., Lobo, Z., Sundström, J. A., Furlong, C. E. and Hall, B. D. 1987. Expression of the *E. coli* xylose isomerase gene in *Saccharomyces cerevisiae*. Appl. Environ. Microbiol. 53, 1996–2000.

Senac, T. and Hahn-Hägerdal, B. (1990) Appl. Environ. Microbiol. 56, 120–126.

Sikorski, R. S. and Hieter, P. (1989) A system of shuttle vectors and yeast host strains designed for efficient manipulation of DNA in *Saccharomyces cerevisiae*. Genetics 122: 19–27.

Skoog, K. and Hahn-Hägerdal, B. (1988) Enzyme Microb. Technol. 10: 66–78.

Slininger, P. J., Bolen, O. L. and Kurtzman, C. P. (1987) Enzyme Microb. Technol. 9: 5–15.

Smiley, K. L. and Bolen, P. L. (1982) Demonstration of D-xylose reductase and D-xylitol dehydrogenase in *Pachysolen tannophilus*. Biotechnol. Lett. 4: 607.

Van Zyl, C., Prior, B. A., Kilian, S. G. and Kock, J. L. F. 1989. D-xylose utilization by *Saccharomyces cerevisiae*. J. Gen. Microbiol. 135, 2791–2798.

Wandrey, C., Wichmann, R., Leuchtenberger, W., Kula, M.-R. and Bückmann, A. F. (1981) U.S. Pat. No 4.304.858.

Wandrey, C., Wichmann, R., Leuchtenberger, W., Kula, M.-R. and Bückmann, A. F. (1982) U.S. Pat. No 4.326.031.

Yoshitake, J., Shimamura, M. and Imai, T. 1973a. Xylitol production by an Enterobacter species. Agr. Biol. Chem. 37, 2261–2267.

Yoshitake, J., Shimamura, M. and Imai, T., 1973b. Xylitol production by a Corynebacterium species. Agr. Biol. Chem. 37, 2251–2259.

Young, R. A. and Davies, R. W. (1983) Yeast RNA polymerase II genes: isolation with antibody probes. Science 222: 778–782.

Yu, S., Wayman, M. and Parehk, S. R. (1987) Biotechnol. Bioeng. 29: 1144–1150.

Zagursky, R. J., Berman, M. L., Baumeister, K. and Lomax, N. (1986) Rapid and easy sequencing of large linear double stranded DNA and supercoiled plasmid DNA. Gene Anal. Techn. 2: 89–94.

Deposited Microorganism

The following yeast strain was deposited according to the Budapest Treaty at the National Collection of Yeast Cultures (NCYC), AFRC Institute of Food Research, Norwich Laboratory, Colney Lane, Norwich, NR4 7UA, UK

| Strain | Deposition number | Deposition date |
| --- | --- | --- |
| *Saccharomyces cerevisiae* VTT-C-91181 carrying the plasmid pMW22 | NCYC 2352 | March 29, 1991 |

We claim:

1. A process for producing ethanol comprising:
(a) isolating from a donor yeast or fungus a first polynucleotide encoding a polypeptide comprising the amino acid sequence of SEQ ID NO:3, or a fragment thereof, wherein the polypeptide or the fragment has xylose reductase activity, and a second polynucleotide encoding a polypeptide comprising the amino acid sequence of SEQ ID NO:7, or a fragment thereof, wherein the polypeptide or the fragment has xylitol dehydrogenase activity;
(b) constructing yeast vectors comprising said polynucleotides;
(c) transforming a yeast host cell with the vectors obtained in step (b) to obtain a recombinant yeast strain;
(d) cultivating said recombinant yeast strain in a xylose containing medium permitting the expression of the first polynucleotide and the second polynucleotide; and
(e) isolating and purifying ethanol formed in the medium.

2. The process of claim 1, wherein
said first polynucleotide comprises the nucleic acid sequence of SEQ ID NO:2 or a fragment thereof, and wherein the second polynucleotide comprises the nucleic acid sequence of SEQ ID NO:6 or a fragment thereof.

3. The process of claim 1, wherein the yeast host is selected from the group consisting of *Saccharomyces cerevisiae,* a *Kluyveromyces* spp., *Schizosaccharomyces pombe* and a *Pichia* spp.

4. The process of claim 3, wherein the yeast host is of the species *Saccharomyces cerevisiae.*

5. A process for producing ethanol comprising:
(a) cultivating a recombinant yeast strain transformed with a first polynucleotide encoding a polypeptide comprising the amino acid sequence of SEQ ID NO:3, or a fragment thereof, wherein the polypeptide or the fragment has xylose reductase activity, and a second polynucleotide encoding a polypeptide comprising the amino acid sequence of SEQ ID NO:7, or a fragment thereof, wherein the polypeptide or the fragment has xylitol dehydrogenase activity, in a xylose-containing medium; and
(b) isolating and purifying ethanol formed in the medium;
wherein said first polynucleotide and second polynucleotide are isolated from a donor yeast or fungus.

6. A process for producing ethanol comprising:
(a) isolating from a donor yeast or fungus a first polynucleotide encoding a polypeptide comprising the amino acid sequence of SEQ ID NO:3, or a fragment thereof, wherein the polypeptide or the fragment has xylose reductase activity, and a second polynucleotide encoding a polypeptide comprising the amino acid sequence of SEQ ID NO:7, or a fragment thereof, wherein the polypeptide or the fragment has xylitol dehydrogenase activity;
(b) constructing yeast vectors comprising said polynucleotides;
(c) transforming a yeast cell having xylose reductase activity and/or xylitol dehydrogenase activity with one of the vectors obtained in step (b) to obtain a recombinant yeast strain having an enhanced ability to utilize xylose;

(d) cultivating said recombinant yeast strain in a xylose containing medium permitting the expression of the polynucleotide as transformed; and (e) isolating and purifying ethanol formed in the medium.

7. A process for producing ethanol comprising:

(a) transforming a host yeast strain with a first polynucleotide encoding a polypeptide comprising the amino acid sequence of SEQ ID NO:3, or a fragment thereof, wherein the polypeptide or the fragment has xylose reductase activity, and/or with a second polynucleotide encoding a polypeptide comprising the amino acid sequence of SEQ ID NO:7, or a fragment thereof, wherein the polypeptide or the fragment has xylitol dehydrogenase activity;

(b) cultivating the recombinant yeast strain transformed as described in step (a) in a xylose-containing medium; and (c) isolating and purifying ethanol formed in the medium.

8. The process of any one of claim 5, 6, or 7, wherein said first polynucleotide comprises the nucleic acid sequence of SEQ ID NO:2 or a fragment thereof, and wherein the second polynucleotide comprises the nucleic acid sequence of SEQ ID NO:6 or a fragment thereof.

9. The process of any one of claim 5, 6, or 7, wherein the yeast host is selected from the group consisting of *Saccharomyces cerevisiae,* a Kluyveromyces spp., *Schizosaccharomyces pombe* and a Pichia spp.

10. The process of claim 9, wherein the yeast host is of the species *Saccharomyces cerevisiae.*

11. A process for producing ethanol comprising:

(a) cultivating *Saccharomyces cerevisiae* H550 in a xylose containing medium; and (b) isolating and purifying ethanol formed in the medium.

* * * * *

UNITED STATES PATENT AND TRADEMARK OFFICE
CERTIFICATE OF CORRECTION

PATENT NO.     : 6,582,944 B1
DATED          : June 24, 2003
INVENTOR(S)    : Johan Hallborn et al.

It is certified that error appears in the above-identified patent and that said Letters Patent is hereby corrected as shown below:

<u>Title page,</u>
Item [73], Assignee, please delete "Xyrofin Oy, Helsinki (FI)" and replace therefor
-- Valtion teknillinen tutkimuskeskus, Espoo (FI) --.

Signed and Sealed this

Thirtieth Day of December, 2003

JAMES E. ROGAN
*Director of the United States Patent and Trademark Office*